US006589047B1

(12) United States Patent
Papai

(10) Patent No.: US 6,589,047 B1
(45) Date of Patent: *Jul. 8, 2003

(54) VENTING PLATE FOR A CONTAINERIZED CANDLE WITH A CHANNELED BAFFLE

(75) Inventor: Tod A. Papai, LaPorte, IN (US)

(73) Assignee: Smith Mountain Properties, LLC., Forest, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/136,538

(22) Filed: May 1, 2002

Related U.S. Application Data

(63) Continuation-in-part of application No. 10/040,121, filed on Jan. 4, 2002.

(51) Int. Cl.[7] .......................... F21L 19/00; F21V 37/02; F21V 35/00
(52) U.S. Cl. ................... 431/291; 431/289; 362/161; 362/163; 362/180
(58) Field of Search ................... 431/288, 291, 431/320, 321, 310, 298, 300; 362/161, 159, 171, 173, 180, 182, 266, 312, 313, 163; 126/43, 44, 45, 1 R, 248, 260, 255, 257, 258, 256, 259 R, 259 M

(56) References Cited

U.S. PATENT DOCUMENTS

| 8,732 A | * | 2/1852 | Bvlaisdell et al. | 126/152 R |
|---|---|---|---|---|
| 142,432 A | * | 9/1873 | Blaisdell et al. | 362/171 |
| 179,548 A | * | 7/1876 | Graves | 362/171 |
| 205,648 A | * | 7/1878 | Irwin | 417/151 |
| 212,603 A | * | 2/1879 | Irwin | 362/171 |
| 214,238 A | * | 4/1879 | Butler | 362/312 |
| 222,663 A | * | 12/1879 | Cash et al. | 362/171 |
| 439,672 A | * | 11/1890 | Miller | |
| 492,954 A | * | 3/1893 | Boesch | 362/180 |
| 493,495 A | * | 3/1893 | Funck | 362/180 |
| 564,882 A | * | 7/1896 | Hamm | 362/171 |
| 595,191 A | * | 12/1897 | Miller et al. | 362/180 |
| 1,097,464 A | * | 5/1914 | Prahm | 362/182 |
| 1,162,682 A | * | 11/1915 | Cherry | 422/126 |
| 1,446,353 A | * | 2/1923 | Slocum | 126/43 |
| 1,540,015 A | * | 6/1925 | Karlson | 362/182 |
| 1,568,465 A | * | 1/1926 | Olsson | 126/93 |
| 1,705,877 A | * | 3/1929 | Ramsey | 362/161 |
| 4,926,298 A | * | 5/1990 | Zimmerman | 169/24 |
| 6,061,950 A | * | 5/2000 | Carey et al. | 422/126 |
| 6,231,336 B1 | * | 5/2001 | Chen | 362/163 |
| 6,382,962 B1 | * | 5/2002 | Papai | 362/163 |

FOREIGN PATENT DOCUMENTS

| DE | 26 18 394 | * | 1/1978 | 431/291 |
|---|---|---|---|---|
| DE | 2925617 | * | 1/1981 | 431/298 |

* cited by examiner

Primary Examiner—Carl D. Price
(74) Attorney, Agent, or Firm—R. Tracy Crump

(57) ABSTRACT

A venting plate for a containerized candle, which improves scent distribution while still providing a clean soot free combustion is disclosed. The venting plate includes a flat disc shaped top and a channeled annular baffle. The venting plate sits atop the mouth of the containerized candle and is supported above the rim of the vessel mouth by a number of mounting bosses or feet. The mounting feet space the top above the candle brim to permit the flow of inlet air underneath the venting plate between the plate top and the brim of the candle vessel. The baffle extends downward into the mouth of the vessel around the exhaust vent and has six recessed longitudinal furrows, which allow inlet air into the vessel interior. The baffle redirects the inlet air flow, which enters the candle horizontally from underneath the venting plate, downward along the vessel sidewall. The inlet air flow passes through the six inlet channels, which columnate the inlet air flow into distinct columns of air. Columnating the inlet air flow increases the velocity of the air flow down the vessel side walls. The increased inlet air flow velocity allows more scent particulate to be picked up as the air flow moves over the melted wax pool towards the flame, thereby promoting improved scent distribution.

4 Claims, 1 Drawing Sheet

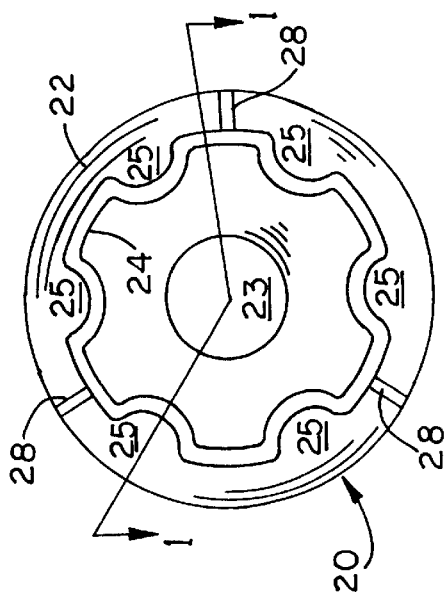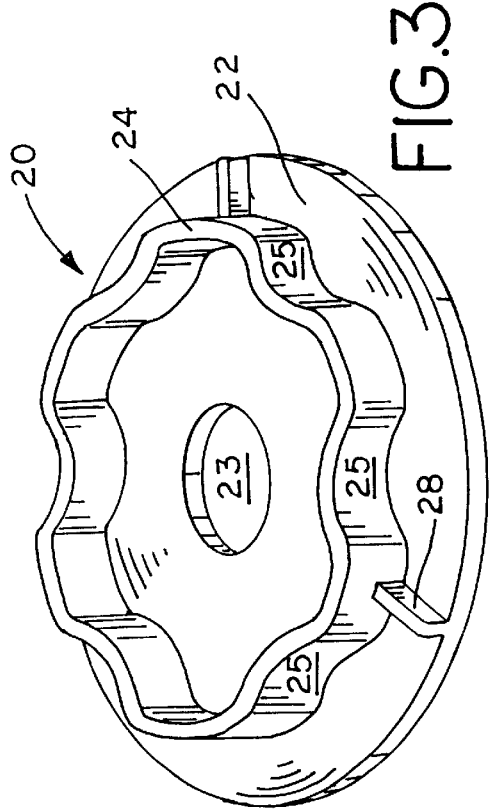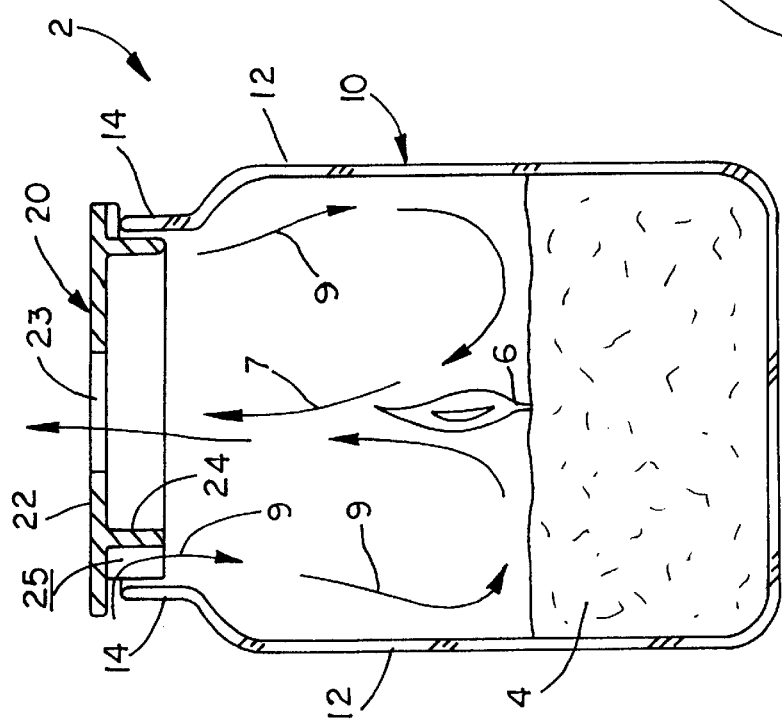

VENTING PLATE FOR A CONTAINERIZED CANDLE WITH A CHANNELED BAFFLE

This a continuation-in-part of pending U.S. patent application, Ser. No. 10/040,121 filed Jan. 4, 2002.

This invention relates to a venting plate for containerized candles, which improves the candle's combustion and eliminates candle smoke, and in particular a venting plate having a channeled baffle or skirt, which increases the air flow velocity to improve scent distribution.

BACKGROUND OF INVENTION

U.S. Pat. No. 6,382,962 granted May 7, 2002 describes a venting plate that is used with apothecary candles to improve the efficiency of the combustion. This venting plate has a central exhaust vent opening and a plurality of peripheral inlet vent openings which are situated to facilitate concentric laminar air flows within the vessel by separation of the cool inlet air from the hot exhaust air.

An improved venting plate for apothecary jar candles has been created by Tod A. Papai of LaPorte, Ind., which is marketed by Smith Mountain Properties, LLC. of Forest Va. This venting plate includes an internal baffle for physically separating the inlet and exhaust air flows within the vessel interior. The venting plate is supported atop the candle by a number of feet which space the plate over the brim of the candle to create an annular inlet vent. The baffle directs inlet air flow downward into the interior of the candle through the inlet vent downward along the sidewalls of the vessel and separates the downward inlet air flow from the upward exhaust air flow.

This venting plate creates an annular curtain of inlet air to the wick; however, the large cross sectional area of the inlet vents creates a relatively slow moving (low velocity) inlet air flow into the candle. Low velocity inlet air flows pick up less scent particulate from the melted wax pool than faster moving air flows. Consequently, it is desirable to increase the velocity of the air flow created by the venting plate, in order to improve the scent distribution of the candle.

SUMMARY OF INVENTION

The venting plate of this invention provides improved scent distribution of a containerized candle while still providing clean soot free combustion. The venting plate includes a flat disc shaped top and a channeled annular baffle. The venting plate sits atop of the candle vessel supported by the mounting feet with the baffle extending downward into the candle mouth. The mounting feet space the top above the candle brim to permit the flow of inlet air underneath the venting plate between the plate top and the brim of the candle vessel. The annular baffle extends downward into the mouth of the vessel around the exhaust vent and has six recessed longitudinal furrow or inlet channels, through which the inlet air flow passes into the vessel interior. The baffle redirects the inlet air flow, which enters the candle horizontally from underneath the venting plate, downward along the vessel sidewall. The inlet air flow passes through the six inlet channels, which columnates the inlet air flow, that is, funnels it into distinct columns of air. Columnating the inlet air flow increases the velocity of the air flow down the vessel side walls. The increased inlet air flow velocity allows more scent particulate to be picked up as the air flow moves over the melted wax pool towards the flame, thereby promoting improved scent distribution. The baffle is also a physical barrier, which separates the opposing air flows (inlet and exhaust) to reduce turbulence within the interior of the vessel and stabilize the flame.

Accordingly, an advantage of the venting plate of this invention is that it provides improved scent distribution.

Another advantage of this invention is that the channeled baffle columnates the inlet air flow into separate columns of air, which increases the inlet air flow velocity and thereby improves scent distributed.

Another advantage is that the venting plate includes an internal baffle for directing inlet air flow downward along the sidewalls of a containerized candle.

Another advantage is that the venting plate stabilizes the combustion flame and improves the efficiency of the combustion of conventional containerized candles, thereby reducing the smoke produced in the combustion process of containerized candles.

Another advantage is that the venting cover reduces turbulence in containerized candles by separating concentric laminar air flow within the candle vessel, which enables sufficient ambient air flow directly to the base of the flame.

Other advantages will become apparent upon a reading of the following description.

BRIEF DESCRIPTION OF THE DRAWINGS

The preferred embodiments of the invention have been depicted for illustrative purposes only wherein:

FIG. 1 is a bottom plan view of the venting plate of this invention;

FIG. 2 is a side sectional view of the venting plate of this invention seated atop a cylindrical containerized candle; and FIG. 3 is a bottom perspective view of the venting plate of this invention;

DESCRIPTION OF THE PREFERRED EMBODIMENT

The preferred embodiment herein described is not intended to be exhaustive or to limit the invention to the precise form disclosed. It is chosen and described to explain the invention so that others skilled in the art might utilize its teachings.

The venting plate of this invention is an improvement on the venting plate of U.S. patent application Ser. No. 10/040,121 filed Jan. 4, 2002, whose teachings are incorporated herein by reference. FIG. 1 shows the venting plate of this invention (designated as reference numeral 20) used on a conventional cylindrical apothecary jar candle (designated generally as reference numeral 2). The venting plate of this invention is intended to be adapted for use with any containerized candle regardless of shape, wick configuration or dimension, and is illustrated with a cylindrical jar candle only for simplicity of explanation and illustration. Candle 2 includes a quantity of wax 4, and one or more cloth or porous wicks 6 contained inside a transparent or translucent glass jar or vessel 10. Vessel 10 includes sidewalls 12 that terminate in a brim 14 forming an open mouth. The size of vessel 10 and the dimensions of its mouth may vary, as well as, its shape within the scope of this invention. Candle wax 4 fills the bottom portion of vessel 10. One or more wicks 6 are seated within the solid wax. When candle 2 is burning, the heat from flame 8 creates a thin layer of melted candle wax across the top of the solid candle wax, which is drawn up the wicks 6 to feed the flame.

Wax 4 is employed in candle 2 as a fuel source and may take any natural unctuous, viscous or solid heat sensitive compound consisting essentially of high molecular weight hydrocarbons or esters of fatty acids. Typically, the candle wax also contains various essential oils to give the wax a pleasant scent and aroma when burned. The gaseous and solid particulate of the essential oils is carried in the combustion exhaust as the wax burns. Ideally, in a clean combustion, soot and smoke are reduced by providing sufficient oxygen to the flame to completely spend the hydrocarbon fuel, while the scent particulate is expelled with the hot exhaust air.

As shown in the figures, venting plate 20 includes a flat disc shaped top 22 and an inset channeled baffle 24. The venting plate of this invention may be constructed from a material, which has thermal insulating properties, such as ceramic, glass, or a heat resistant plastic. Ideally, these materials, glass, ceramic and plastics are easily formed and molded. Although, glass, ceramic and plastics are highly desirable construction materials, the venting plates may also be constructed from metals, and other suitable materials without deviating from the principal teachings of this invention. Top 22 has circular central exhaust opening or vent 23. Top 22 is illustrated as a planar circular disc, but may be conical or domed in shape as desired. Exhaust vent 23 is illustrated as having a circular shape, but may be shaped in any desirable configuration, without deviating from the teachings of this invention. Typically, the diameter of the exhaust vent ranges between 0.5 and 2.0 inches, which is generally ideal for venting exhaust air from the combustion of conventional candle wax. As best shown in FIGS. 2 and 3 (both bottom views of venting plate 20), baffle 24 is a vertical skirt, which extends downward from top 22 around exhaust vent 23. Baffle 24 is inset from the peripheral edge of top 22 and mirrors the inner contour of brim 14. The outer diameter of baffle 24 is dimensioned to abut directly adjacent to the inner face of the candle brim. Baffle 24 has six longitudinal furrows, which form six air flow inlet channels or vents 25. Venting plate 20 also includes three mounting bosses or feet 28 extending downward from its bottom face. Feet 28 extend radially from baffle 24 to the outer edge of top 22 at equally spaced locations approximately 120 degrees apart.

Operation

FIG. 1 illustrates how venting plate 20 creates a physically separated concentric laminar air flow within interior 17 of vessel 10, which stabilizes the flame and improves the efficiency of the combustion. As shown in FIG. 1, venting plate 20 sits atop of candle 2 supported by mounting feet 28, such that baffle 24 extends downward into the candle mouth. Mounting feet 28 support the venting plate atop candle 2 such that top 22 is spaced vertically above the candle brim 14. The distance between the venting plate and candle brim ranges between 1/16 and 3/8 of an inch. Exhaust vent 23 is positioned directly above flame 8. The thermal energy generated from flame 8 creates an upward convection flow of hot exhaust air 7, which exits the candle interior through exhaust vent 23. Positioning the exhaust vent directly above the candle flame focuses the convection draft of exhaust air flow 7 directly upwards, which reduces diffusion of the exhaust flow and its thermal energy. The negative pressure within the candle interior created by exhaust air flow 7 draws an inlet air flow 9 of cool ambient air underneath plate 20 between top 22 and vessel brim 14. Baffle 24 redirects inlet air flow 9, which enters the candle horizontally from underneath the venting plate, downward along vessel sidewall 12. Inlet air flow 9 passes through six inlet channels 25, which columnate the inlet air flow into distinct columns of air, which results in an increased inlet air flow velocity. The columns of inlet air move along the melted wax pool and converge at the base of the candle flame. Baffle 24 also separates the opposing air flows (inlet and exhaust) to reduce turbulence within the interior of the vessel and stabilize the flame, which leads to a cleaner combustion process and reduced carbon residue (smoke) in the exhaust.

Advantages

One skilled in the art will note several advantages of the venting plates of this invention over the venting plates of U.S. Pat. No. 6,382,962 and U.S. patent application Ser. No. 09/925,893. The venting plate of this invention, stabilizes the combustion flame and improves the efficiency of the combustion of conventional containerized candles, thereby reducing the smoke produced in the combustion process of containerized candles. In addition, the channeled baffle provides a physical barrier that reduces turbulence in containerized candles by separating concentric laminar air flow within the candle vessel, which enables sufficient ambient air flow directly to the base of the flame. More importantly, the channeled baffle allows the inlet air flow to be columnated into six separate columns of air within the candle vessel. Columnating the inlet air flow increases the velocity of the air flow, down the sidewalls of the candle and over the melted wax pool toward the flame. Increasing the velocity of the inlet air flow over the melted wax pool improves scent distribution. The fast moving inlet air flow picks up more scent particulate, which will eventually be expelled with the exhaust air. As a result the venting plate of this invention facilitates the distribution of a strong aroma from the jar candle.

It is understood that the above description does not limit the invention to the details given, but may be modified within the scope of the following claims.

I claim:

1. A venting apparatus (20) for improving the stability and efficiency of the combustion flame of a containerized candle that includes a fuel source burnt in the flame, a wick and a vessel (10), which defines an interior thereof for enclosing the wick and fuel source and has an open mouth, and where the vessel includes sidewalls (12) that terminate in a brim (14) at the open mouth of the vessel, the venting apparatus comprising:

a flat top (22) shaped and dimensioned to cover the open mouth (15) of the vessel (10) and extend over the brim, the top having an exhaust vent (23) therein for venting a flow of exhaust air from the vessel interior, a plurality of feet (28) extending downward from the top for spacing the top above the brim when the venting apparatus is seated atop the vessel to permit a flow of inlet air between the top and the vessel brim, and an annular baffle (24) extending downward from the top between the plurality of feet and the exhaust venting means so as to extend partially downward into the open mouth of the vessel and to seat adjacent the brim of the vessel when the apparatus is seated atop the vessel, the baffle constitutes means for directing the flow of inlet air downward along the sidewalls of the vessel and for separating the flow of inlet air from the flow of exhaust air, the baffle having a plurality of longitudinal inlet channels (25) radially spaced along the periphery of the baffle so as to form inlet openings through which inlet air may enter the vessel interior, the plurality of channels constituting means for columnating the flow of inlet air into a plurality of distinct and radially spaced and separated air flow columns within the vessel interior.

2. The apparatus of claim 1 wherein the exhaust venting (23) is located directly over the flame of the containerized candle when the cover is seated atop the candle vessel and the containerized candle burns.

3. In combination, a containerized candle (2) and a venting apparatus (20) for improving the stability and efficiency of the combustion flame of the containerized candle, the containerized candle includes a fuel source burnt in the flame, a wick and a vessel (10), which defines an interior thereof for enclosing the wick and fuel source and has an open mouth, and where the vessel includes sidewalls (12) that terminate in a brim (14) at the open mouth of the vessel, the venting plate comprising:
- a flat top (22) shaped and dimensioned to cover the open mouth of the vessel (10) and extend over the brim of the vessel, the top having an exhaust vent (23) therein for venting a flow of exhaust air from the vessel interior,
- a plurality of feet (28) extending downward from the top for spacing the top above the brim when the venting apparatus is seated atop the vessel to permit a flow of inlet air between the top and the vessel brim, and
- an annular baffle (24) extending downward from the top between the plurality of feet and the exhaust venting means so as to extend partially downward into the open mouth of the vessel and to seat adjacent the brim of the vessel when the apparatus is seated atop the vessel, the baffle constitutes means for directing the flow of inlet air downward along the sidewalls of the vessel and for separating the flow of inlet air from the flow of exhaust air, the baffle having a plurality of longitudinal inlet channels (25) radially spaced along the periphery of the baffle so as to form inlet openings through which inlet air may enter the vessel interior, the plurality of channels constituting means for columnating the flow of inlet air into a plurality of distinct and radially spaced and separated air flow columns within the vessel interior.

4. The combination of claim 3 wherein the exhaust venting (23) is located directly over the flame of the containerized candle when the cover is seated atop the candle vessel and the containerized candle burns.

* * * * *